(12) United States Patent
Shinji

(10) Patent No.: US 10,564,411 B2
(45) Date of Patent: Feb. 18, 2020

(54) ILLUMINATION DEVICE AND ENDOSCOPE

(71) Applicant: OLYMPUS CORPORATION, Hachioji-shi, Tokyo (JP)

(72) Inventor: Sho Shinji, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 313 days.

(21) Appl. No.: 15/613,074

(22) Filed: Jun. 2, 2017

(65) Prior Publication Data

US 2017/0269348 A1 Sep. 21, 2017

Related U.S. Application Data

(63) Continuation of application No. PCT/JP2014/082307, filed on Dec. 5, 2014.

(51) Int. Cl.
*F21V 8/00* (2006.01)
*G02B 23/24* (2006.01)
(Continued)

(52) U.S. Cl.
CPC ...... *G02B 23/2469* (2013.01); *A61B 1/00096* (2013.01); *A61B 1/00165* (2013.01); (Continued)

(58) Field of Classification Search
CPC .. A61B 1/0669; A61B 1/0684; F21V 33/0068
(Continued)

(56) References Cited

U.S. PATENT DOCUMENTS 7,597,467 B2 10/2009 Itaya
2002/0015314 A1 2/2002 Umemoto et al.
(Continued)

FOREIGN PATENT DOCUMENTS

CN 1896839 A 1/2007
EP 2469322 A1 6/2012
(Continued)

OTHER PUBLICATIONS

Chinese Office Action (and English language translation thereof) dated Jan. 11, 2019 issued in counterpart Chinese Application No. 201480083037.3.
(Continued)

*Primary Examiner* — William J Carter
(74) *Attorney, Agent, or Firm* — Holtz, Holtz & Volek PC

(57) ABSTRACT

An illumination device comprises: an optical member that is provided with a circular ring-shaped or horseshoe-shaped light-guiding layer and diffusion layer, which are laminated in a central axis direction, the light-guiding layer having a light-entrance surface facing a tangential direction; and a light-introducing member that is disposed at the radially outer side of the optical member and that introduces illumination light into the light-guiding layer from the light-entrance surface, in the tangential direction; wherein the diffusion layer diffuses the illumination light entering from the light-guiding layer by volume scattering, and the optical member is formed, at least, of one end surface in the axial direction and emits the illumination light emitted from the diffusion layer.

22 Claims, 12 Drawing Sheets

(51) Int. Cl.
G02B 23/26 (2006.01)
G03B 15/05 (2006.01)
A61B 1/00 (2006.01)
A61B 1/06 (2006.01)

(52) U.S. Cl.
CPC .......... *A61B 1/0607* (2013.01); *G02B 6/0051* (2013.01); *G02B 23/2423* (2013.01); *G02B 23/26* (2013.01); *G03B 15/05* (2013.01); *G03B 2215/0575* (2013.01)

(58) Field of Classification Search
USPC ........................................................ 362/574
See application file for complete search history.

(56) References Cited

U.S. PATENT DOCUMENTS

| 2006/0139946 | A1* | 6/2006 | Tamaki ................ G02B 6/0018 362/602 |
| 2007/0014110 | A1 | 1/2007 | Itaya |
| 2007/0189352 | A1* | 8/2007 | Nagahama ........... A61B 1/0653 372/71 |
| 2012/0134159 | A1 | 5/2012 | Kamo et al. |
| 2013/0137923 | A1* | 5/2013 | Honda ............... G02B 23/2469 362/574 |
| 2014/0347878 | A1 | 11/2014 | Honda et al. |

FOREIGN PATENT DOCUMENTS

| EP | 2649923 | A1 | 10/2013 |
| EP | 2815691 | A1 | 12/2014 |
| JP | 2002071965 | A | 3/2002 |
| JP | 2014094122 | A | 5/2014 |
| JP | 5526011 | B2 | 6/2014 |
| WO | 2011058912 | A1 | 5/2011 |
| WO | 2012137737 | A1 | 10/2012 |
| WO | 2014073426 | A1 | 5/2014 |

OTHER PUBLICATIONS

International Search Report (ISR) and Written Opinion dated Mar. 3, 2015 issued in International Application No. PCT/JP2014/082307.

* cited by examiner

ND ENDOSCOPE

CROSS-REFERENCE TO RELATED APPLICATIONS

This is a continuation of International Application PCT/JP2014/082307 which is hereby incorporated by reference herein in its entirety.

TECHNICAL FIELD

The present invention relates to an illumination device and an endoscope.

BACKGROUND ART

In the related art, a known illumination device provided at the distal end of an endoscope uses a C-ring-shaped light-guiding member disposed around an imaging optical system (for example, see Patent Literature 1). To observe an observation target site in detail with an endoscope, there are cases where the distal end surface of the endoscope is brought into contact with the observation target site. At that time, when the distal end surface of the endoscope is disposed at an angle with respect to the surface of the observation target, the distance between the lower portion of the distal end surface of the endoscope and the observation target site decreases, and the illumination light becomes partially brighter, thus causing halation in the lower region in the endoscope image. In Patent Literature 1, halation is prevented by using a C-ring-shaped light-guiding member, a part of which is removed at the lower side of the distal end surface of the endoscope.

Furthermore, in the illumination device in Patent Literature 1, a reflection surface having an indentation/projection structure is provided on a back surface located on the opposite side from the emission surface of the light-guiding member, and the illumination light guided in the light-guiding member is reflected in various directions by this reflection surface, whereby the illumination light is efficiently emitted from the emission surface.

CITATION LIST

Patent Literature

{PTL 1}
PCT International Publication No. WO 2012/137737

SUMMARY OF INVENTION

A first aspect of the present invention is an illumination device comprising: an optical member that is provided with a circular ring-shaped or horseshoe-shaped light-guiding layer and diffusion layer, which are laminated in a central axis direction, the light-guiding layer having a light-entrance surface facing a tangential direction of the light-guiding layer; and a light-introducing member that is disposed at the radially outer side of the optical member and that introduces illumination light into the light-guiding layer from the light-entrance surface in the tangential direction; wherein the diffusion layer diffuses the illumination light entering from the light-guiding layer by volume scattering in the interior thereof, and the optical member is formed, at least, of one end surface in the central axis direction and has, at least, an emission surface that emits the illumination light emitted from the diffusion layer in the central axis direction.

DESCRIPTION OF EMBODIMENTS

An illumination device 4 and an endoscope 1 provided with the same, according to an embodiment of the present invention, will be described below with reference to the drawings.

Figure 1:
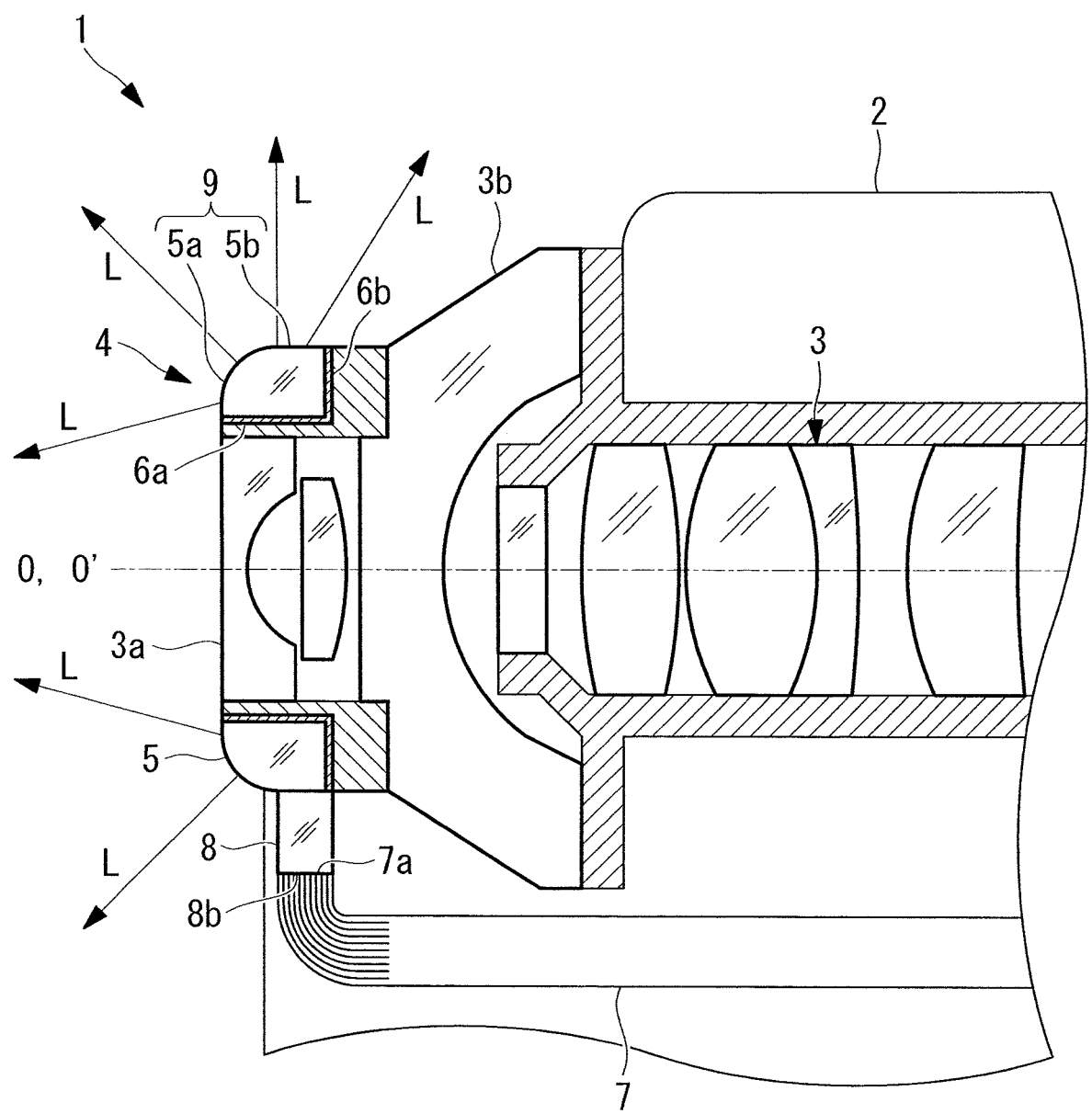
FIG. 1 is a longitudinal sectional view showing a distal end of an endoscope according to an embodiment of the present invention.

As shown in FIG. 1, the endoscope 1 according to this embodiment includes elongated insertion portion 2 that can be inserted inside a body, and an imaging optical system 3 and an illumination device 4 that are provided at the distal end of the insertion portion 2.

The imaging optical system 3 includes a direct-viewing observation window 3a that is disposed in the distal end surface of the insertion portion 2 and that receives light from the front side of an optical axis O' thereof, and a side-viewing viewing observation window 3b that is disposed in the outer circumferential surface of the insertion portion 2 and that receives light from the lateral side of the optical axis O' thereof. Accordingly, the imaging optical system 3 can observe both the front and the sides with respect to the optical axis O'.

The illumination device 4 is provided at the distal end of the insertion portion 2 and is used for viewing straight ahead of the insertion portion 2. The illumination device 4 includes a circular ring-shaped optical member 5, reflecting portions 6a and 6b disposed on an inner circumferential surface and a proximal-end surface of the optical member 5, and a light-guiding member (light-introducing member) 8 that is provided at the outer side in the radial direction of the optical member 5 and that introduces the illumination light L supplied from a light guide 7 into the optical member 5.

The optical member 5 is disposed around the imaging optical system 3 so that a central axis O of the optical member 5 is approximately aligned with the optical axis O' of the imaging optical system 3. A distal end surface 5a and an outer circumferential surface 5b of the optical member 5 are smoothly continuous via a curved surface formed by rounding off the corner between the distal end surface 5a and the outer circumferential surface 5b. Of the surfaces of the optical member 5, only the distal end surface 5a and the outer circumferential surface 5b disposed at the distal end surface of the insertion portion 2 are exposed to the outer side, and the distal end surface 5a and the outer circumferential surface 5b constitute an emission surface 9 from which the illumination light L supplied from the light-guiding member 8 is emitted to the outside.

Figure 2A:
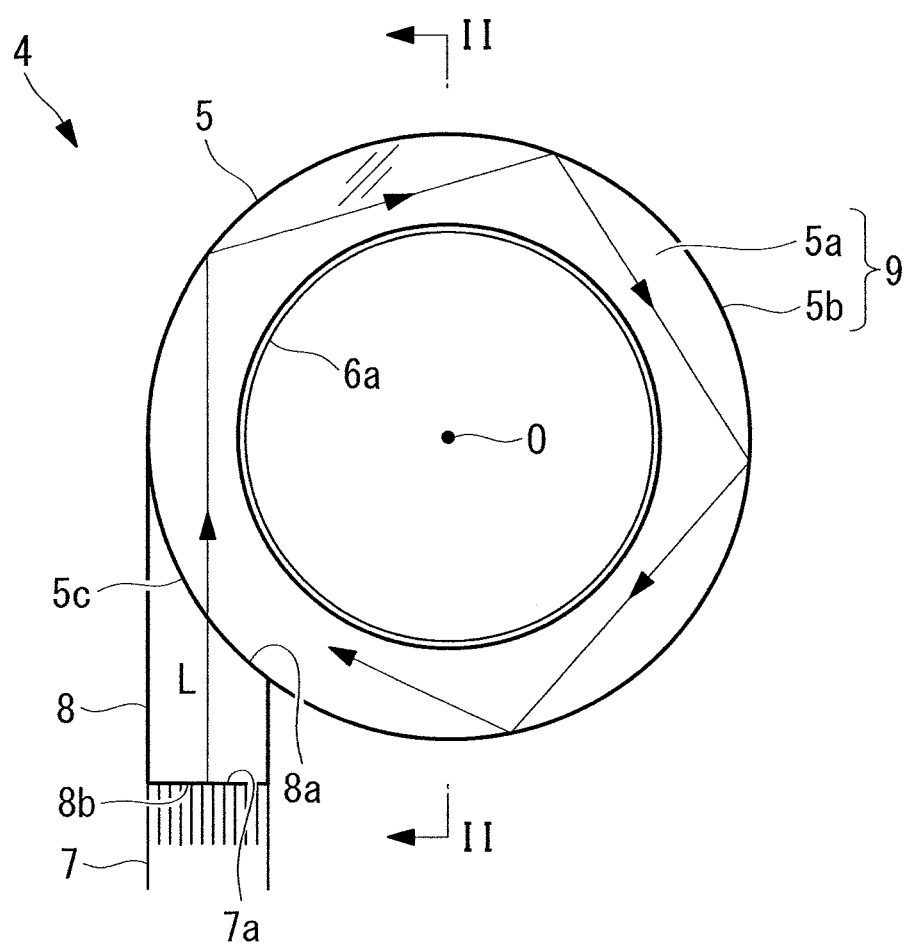
FIG. 2A is a front view, taken from the distal end side, of an illumination device in the endoscope in FIG. 1
Figure 2B:
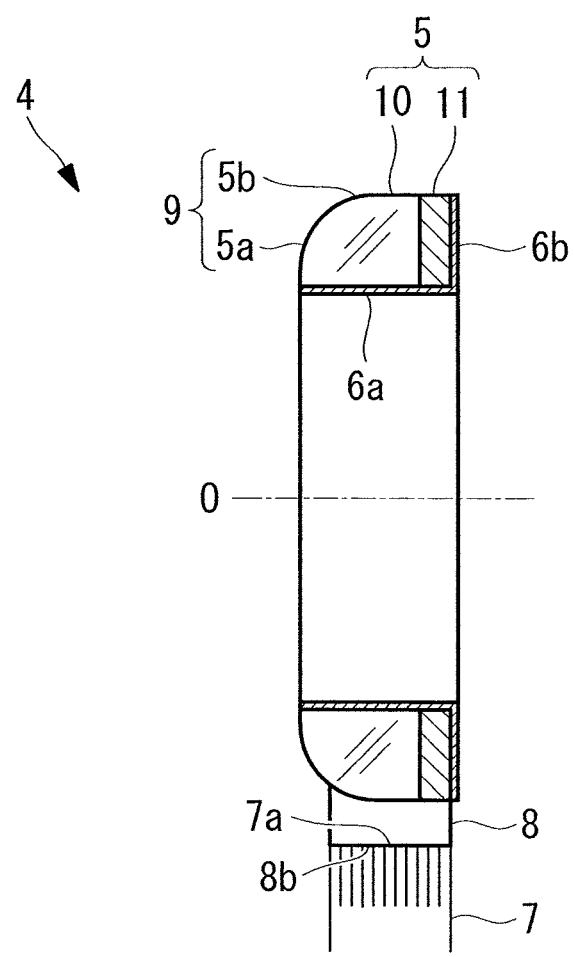
FIG. 2B is a cross-sectional view taken along line II-II in the illumination device in FIG. 2A.

As shown in FIG. 2A and FIG. 2B, the optical member 5 has a two-layer structure in which a circular ring-shaped light-guiding layer 10 and a circular ring-shaped diffusion layer 11 are directly laminated on each other, in this order from the distal end. Therefore, the emission surface 9 is formed from the end surface at the distal end of the light-guiding layer 10 and the outer circumferential faces of the light-guiding layer 10 and the diffusion layer 11. The illumination light L can come and go in the central axis O direction between the light-guiding layer 10 and the diffusion layer 11.

The light-guiding layer 10 has a three-dimensional shape having thickness in the central axis O direction. The light-guiding layer 10 is formed of a transparent medium (for example, polycarbonate or a cyclolefin copolymer) having high transmittance to the illumination light L.

The diffusion layer 11 has a three-dimensional shape having thickness in the central axis O direction. The diffusion layer 11 is formed of the same transparent medium as the transparent medium forming the light-guiding layer 10 and a large number of fine particles (minute regions) that are formed of a material having a different refractive index from that of this transparent medium (for example, titanium oxide) and that are dispersed in the transparent medium. The illumination light introduced into the diffusion layer 11 repeatedly propagates in the transparent medium and is reflected at the interface between the transparent medium and the fine particles, thereby undergoing volume scattering inside the diffusion layer 11. The medium of the diffusion layer 11 may be a medium of a different material from that of the transparent medium constituting the light-guiding layer 10.

The particle diameter $\phi$ (nm) of the fine particles and the particle density $\sigma$ (weight %) of the fine particles satisfy conditional expressions (1) and (2) below. By satisfying conditional expressions (1) and (2), the propagation efficiency of the illumination light L in the diffusion layer 11 and the scattering efficiency at the fine particles are compatible with each other, and it is possible to obtain a high diffusion effect with respect to the illumination light L.

$$100 \leq \phi \leq 500 \quad (1)$$

$$0.2 \leq \sigma \leq 0.5 \quad (2)$$

If the particle diameter $\phi$ exceeds 500 nm, even if the particle density satisfies conditional expression (2), the number of particles per unit volume in the diffusion layer 11 is small. In such a case, or in the case where the particle density $\sigma$ is less than 0.2, the scattering efficiency of the fine particles with respect to the illumination light L becomes weak, and the diffusion efficiency with respect to the illumination light L becomes insufficient. On the other hand, in the case where the particle diameter $\phi$ is less than 100 nm, even if the particle density satisfies conditional expression (2), the number of particles per unit volume is large. In such a case, or in the case where the particle density $\sigma$ exceeds 0.5, the scattering efficiency of the fine particles with respect to the illumination light L becomes too strong, and the illumination light entering the diffusion layer 11 from the light-guiding layer 10 is diffused into the light-guiding layer 10 in the vicinity of the interface with the light-guiding layer 10, and thus, the brightness uniformity in the circumferential direction of the entire optical member 5 decreases.

The thickness T (mm) of the optical member 5 in the central axis O direction and the thickness $\tau$ (mm) of the diffusion layer 11 in the central axis O direction satisfy conditional expression (3) below. By satisfying conditional expression (3), it is possible to achieve both a brightness-uniformizing effect in the circumferential direction of the illumination light L with the light-guiding layer 10 and a diffusion effect of the illumination light L with the diffusion layer 11.

$$0.075 \leq \tau/T \leq 0.3 \quad (3)$$

When $\tau/T$ is less than 0.075, the diffusion layer 11 becomes too thin, and the diffusion effect of the illumination light L by the diffusion layer 11 is insufficient. On the other hand, when $\tau/T$ exceeds 0.3, the light-guiding layer 10 becomes too thin, making it difficult to uniformly guide the illumination light L around the entire circumference of the light-guiding layer 10, and the brightness uniformity of the illumination light L in the circumferential direction of the optical member 5 decreases.

The reflecting portion 6a is, for example, a circular ring-shaped reflecting film or a reflecting membrane deposited on the inner circumferential surface of the optical member 5 and coats the entire inner circumferential surface of the optical member 5. The reflecting portion 6b is, for example, a flat reflecting film or a reflecting membrane that is deposited on the proximal-end surface and covers the entire proximal-end surface of the optical member 5. The reflecting portions 6a and 6b have high reflectances with respect to the illumination light L, reflect the illumination light L emitted in the radially inward direction and the rearward direction from the light-guiding layer 10 and the diffusion layer 11, respectively, and cause the illumination light to re-enter the light-guiding layer 10 and the diffusion layer 11. Accordingly, substantially all of the illumination light L supplied to the optical member 5 from the light-guiding member 8 is emitted from the emission surface 9.

The light-guiding member 8 is a columnar member that extends in the tangential direction of the optical member 5 and is formed of the same transparent medium as the transparent medium forming the light-guiding layer 10. An emission portion 8a formed of one of the end faces in the longitudinal direction of the light-guiding member 8 is connected to at least the outer circumferential surface of the light-guiding layer 10 in the optical member 5. In other words, in the outer circumferential surface of the optical member 5, the region contacting the emission portion 8a and facing the tangential direction constitutes a light-entrance surface 5c for introducing the illumination light L to the optical member 5. The optical member 5 and the light-guiding member 8 may be integrally formed as a single member having an approximately ρ-shaped form.

An entrance portion 8b formed of the other end surface of the light-guiding member 8 is connected to an emission end surface 7a at the distal end of the light guide 7 provided in the longitudinal direction inside the insertion portion 2. The illumination light L entering an entrance end surface (not illustrated) at the proximal end of the light guide 7 from a light source device (not illustrated) enters the light-guiding member 8 from the emission end surface 7a of the light guide 7 via the entrance portion 8b and, furthermore, enters the optical member 5 from the emission portion 8a of the light-guiding member 8 via the light-entrance surface 5c. Accordingly, the illumination light L enters at least the light-guiding layer 10 of the optical member 5 in the tangential direction from the radially outer side along a plane approximately perpendicular to the central axis O.

Next, the operation of the illumination device 4 and the endoscope 1 configured in this way will be described.

The illumination light L that has entered the light-guiding layer 10 of the optical member 5 in the tangential direction via the light guide 7 and the light-guiding member 8 from the light source device is guided in the circumferential direction of the light-guiding layer 10 while undergoing repeated total reflection at the outer circumferential surface of the light-guiding layer 10. Here, the illumination light L is emitted from the emission end surface 7a of the light guide 7 in the form of diffuse light, and therefore, part of the illumination light that has entered the light-guiding layer 10 has a velocity component also in the central axis O direction. Also, the illumination light L is considered to have a velocity component in the central axis O direction when reflected at the curved surface between the distal end surface 5a and the outer circumferential surface 5b of the optical member 5. Therefore, the illumination light L enters the diffusion layer 11 adjacent to the light-guiding layer 10 after being guided in the circumferential direction of the light-guiding layer 10.

In the diffusion layer 11, after the illumination light L is diffused in various directions as a result of volume scattering, a part thereof is emitted to the outside from the outer circumferential surface of the diffusion layer 11 and illuminates the lateral viewing field of the imaging optical system 3, and the majority thereof re-enters the light-guiding layer 10. Of the illumination light L that has re-entered the light-guiding layer 10, the part thereof that has a large velocity component in the central axis O direction due to the volume scattering in the diffusion layer 11 is emitted in the form of a ring without being totally reflected from the distal end surface 5a of the light-guiding layer 10, and illuminates mainly the front viewing field of the imaging optical system 3. Of the illumination light L that has re-entered the light-guiding layer 10, the part thereof that has a large velocity component in the radial direction due to the volume scattering in the diffusion layer 11 is emitted in a radiating form without being totally reflected from the outer circumferential surface of the light-guiding layer 10, and illuminates mainly the lateral viewing field of the imaging optical system 3.

In this way, according to this embodiment, the illumination light L that has entered the optical member 5 from the light-guiding member 8 is first guided in the circumferential direction in the light-guiding layer 10, whereby the brightness of the illumination light L in the optical member 5 is made uniform in the circumferential direction. Furthermore, the illumination light L is diffused by volume scattering in the diffusion layer 11, whereby the brightness of the illumination light becomes even more uniform. Accordingly, an advantage is afforded in that it is possible to illuminate the front viewing field and the lateral viewing field of the imaging optical system 3 with the illumination light having a uniform brightness, which is emitted from the emission surface 9.

Furthermore, if the diffusion layer 11 were disposed at the distal end, and the light-guiding layer 10 were disposed at the proximal end, the illumination light at the light-entrance surface 5c side becomes bright, and the brightness of the illumination light L in the optical member 5 becomes non-uniform in the circumferential direction. According to this embodiment, by disposing the light-guiding layer 10 having an effect of making the brightness of the illumination light L uniform in the circumferential direction at the distal end, an advantage is afforded in that it is possible to emit the illumination light L, having a uniform brightness in the circumferential direction, towards the front.

Also, by means of the reflecting portions 6a and 6b which are disposed on the inner circumferential surface and the proximal-end surface of the optical member 5, substantially the entirety of the illumination light L that has entered the optical member 5 contributes to the illumination of the front viewing field and the lateral viewing field of the imaging optical system 3. Accordingly, an advantage is afforded in that it is possible to improve the illumination light ratio.

Also, if the optical member 5 has a corner between the distal end surface 5a and the outer circumferential surface 5b, nonuniformity occurs in the brightness of the illumination light L due to this corner; however, by having a curved surface between the distal end surface 5a and the outer circumferential surface 5b, it is possible to make the brightness of the illumination light more uniform. Furthermore, entry into the diffusion layer 11 of illumination light L which is guided in the circumferential direction in the light-guiding layer 10 is facilitated by this curved surface, and the emission efficiency of the illumination light L from the emission surface 9 is improved. Accordingly, an advantage is afforded in that the illumination light ratio can be further improved.

Figure 3A:
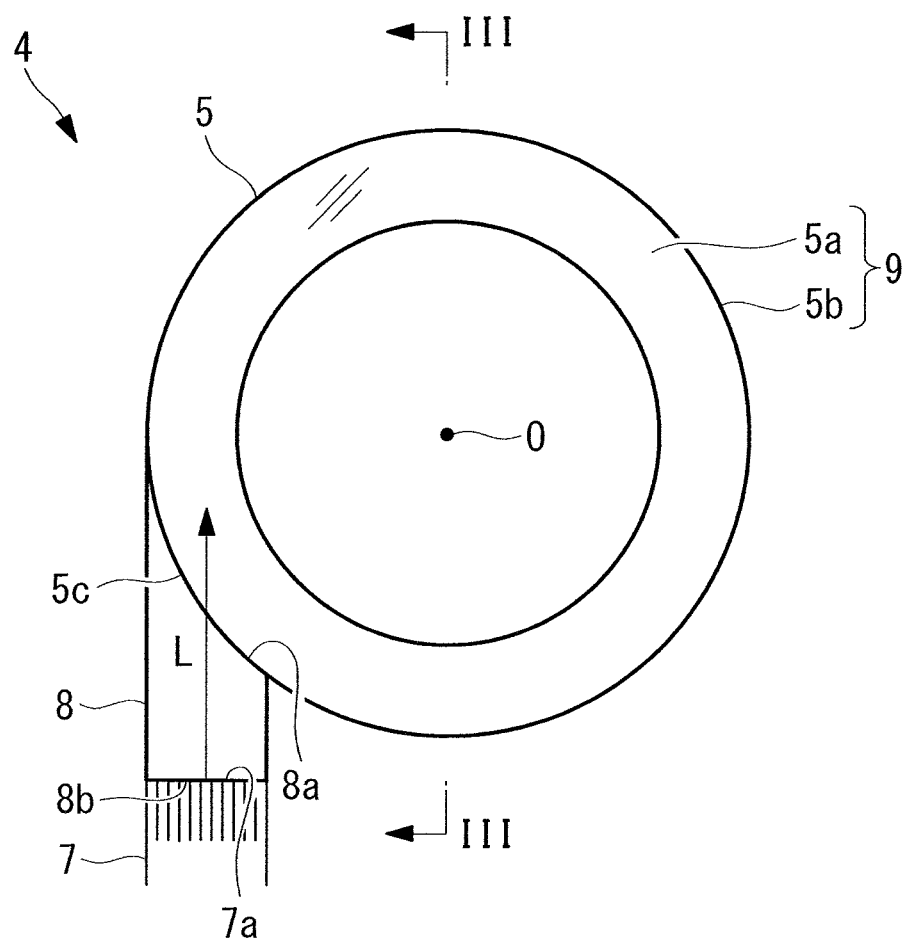
FIG. 3A is a front view, taken from the distal end side, showing a modification of the illumination device in FIG. 2A.
Figure 3B:
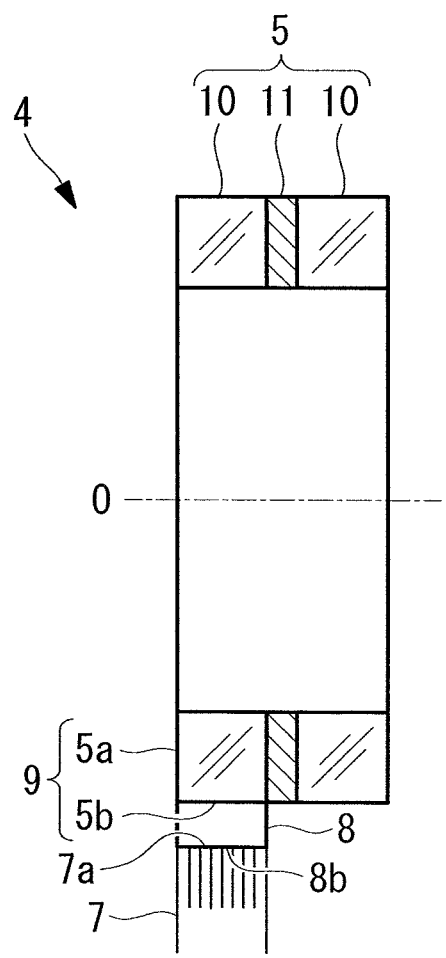
FIG. 3B is a cross-sectional view taken through line III-III in the illumination device in FIG. 3A.

In this embodiment, although it has been assumed that the reflecting portions 6a and 6b are provided on the inner circumferential surface and the proximal-end surface of the optical member 5, instead of this, as shown in FIGS. 3A and 3B, the reflecting portions 6a and 6b may be omitted. Alternatively, the reflecting portion 6a or 6b may be provided on only one of the inner circumferential surface and the proximal-end surface. For example, in the case where the member adjacent to the inner circumferential surface and the proximal-end surface of the optical member 5 has a high reflectance, by using this adjacent member in place of the reflecting portions 6a and 6b, it is possible to omit the reflecting portions 6a and 6b.

In addition, in this embodiment, it has been assumed that the light-guiding member 8 is provided with a single light-guiding layer 10 and a single diffusion layer 11; however, the numbers of light-guiding layers 10 and the diffusion layers 11 can be changed as appropriate. For example, as shown in FIG. 3B, one more light-guiding layer 10 may be provided at the proximal end side of the diffusion layer 11. In this case, the light-guiding member 8 may introduce the illumination light L into either one of the light-guiding layer 10 at the distal end side and the light-guiding layer 10 at the proximal end side.

In addition, in this embodiment, although it has been assumed that the corner between the distal end surface 5a and the outer circumferential surface 5b of the optical member 5 is rounded off, instead of this, as shown in FIG. 3B, the corner may be left as is.

Figure 4A:
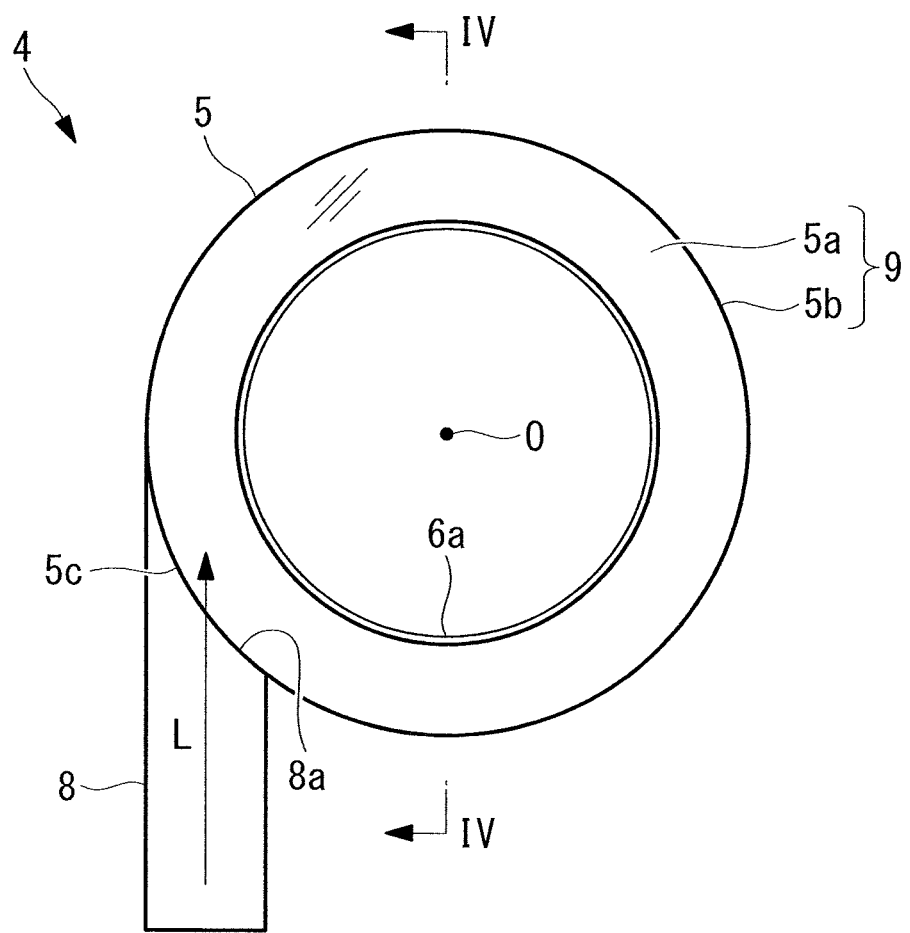
FIG. 4A is front view, taken from the distal end side, showing another modification of the illumination device in FIG. 2A.
Figure 4B:
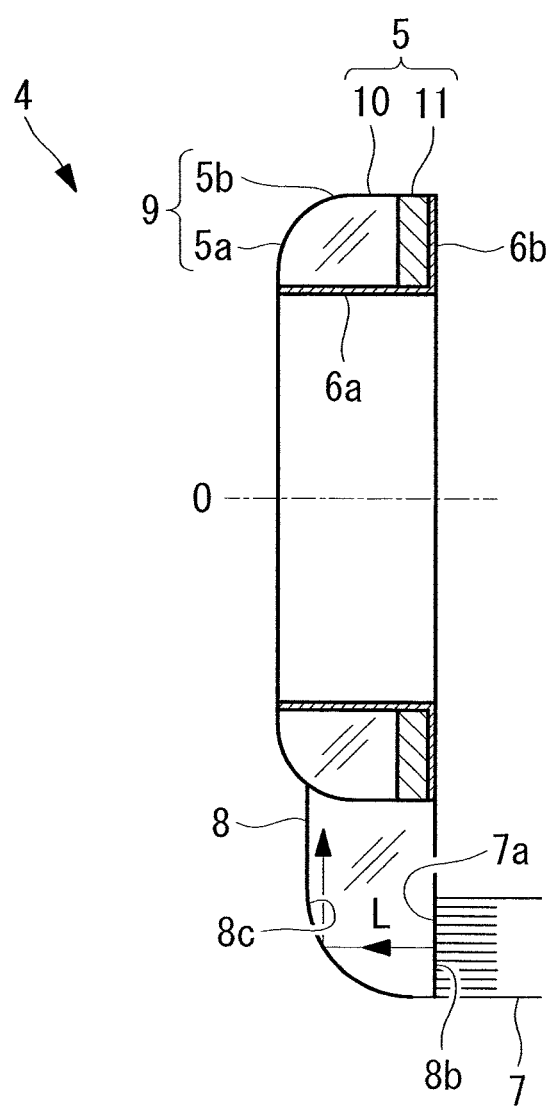
FIG. 4B is a cross-sectional view taken along line IV-IV in the illumination device in FIG. 4A.

Moreover, in this embodiment, it has been assumed that the entrance portion 8b of the light-guiding member 8 is disposed on a tangent of the optical member 5, so that the illumination light L enters the light guiding member 8 in the tangential direction of the optical member 5; however, instead of this, as shown in FIGS. 4A and 4B, the light guiding member 8 may have the entrance portion 8b at the proximal end, so that the illumination light L enters the light-guiding member 8 from the light guide 7 in approximately the central axis O direction. By doing so, the distal end of the light guide 7 can be disposed straight along the optical axis O without being bent.

In this case, the light-guiding member 8 is provided with a deflecting portion 8c that deflects, in the tangential direction of the optical member 5, the illumination light L that has entered from the proximal end side in the central axis O direction. In FIGS. 4A and 4B, the deflecting portion 8c is formed by rounding off the corner between the end surface at the distal end of the light-guiding member 8 and the end surface at the other end in the longitudinal direction, and is formed of a curved surface that reflects the illumination light L that has entered in approximately the central axis O direction towards the light-guiding member 8.

Moreover, in this embodiment, although it has been assumed that the light-guiding member 8 introduces the illumination light L into the optical member 5 in one direction; instead of this, the illumination light L may be introduced into the light-guiding layer 10 in two directions so as to be guided in two mutually opposite directions.

Figure 5A:
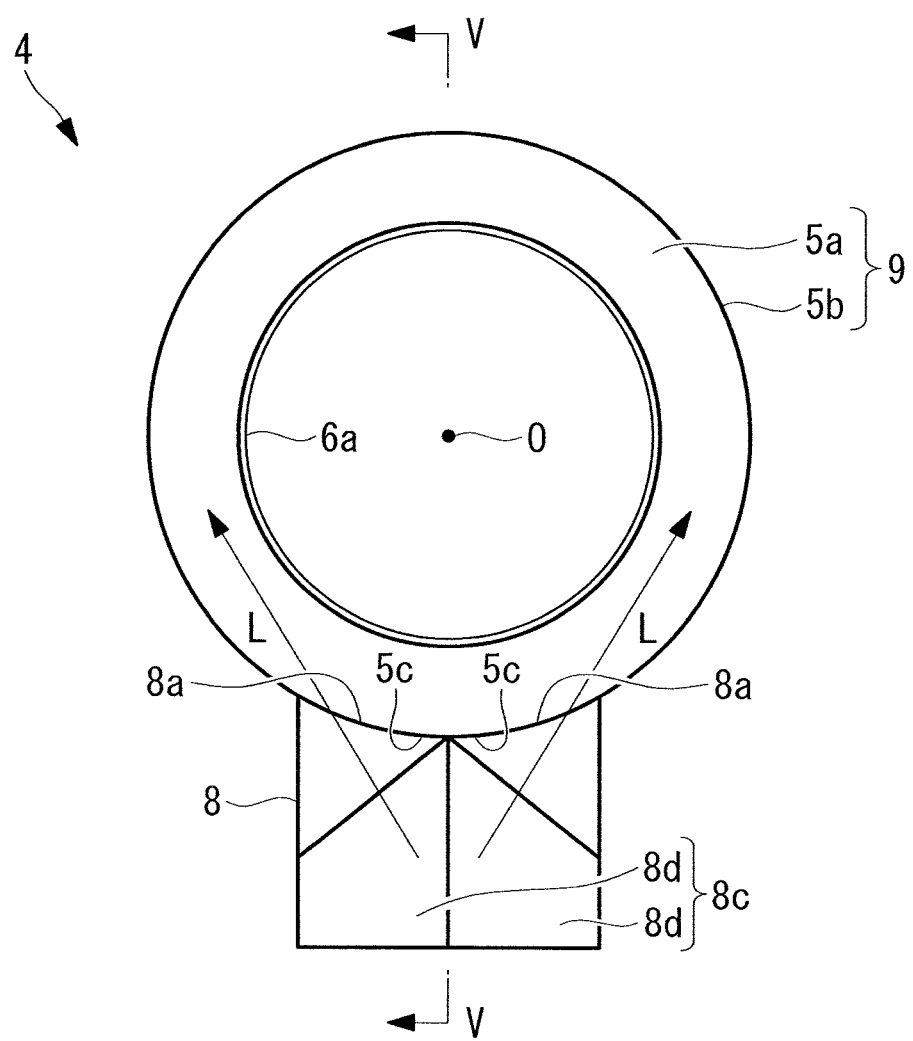
FIG. 5A is a front view, taken from the distal end side, showing another modification of the illumination device in FIG. 2A.
Figure 5B:
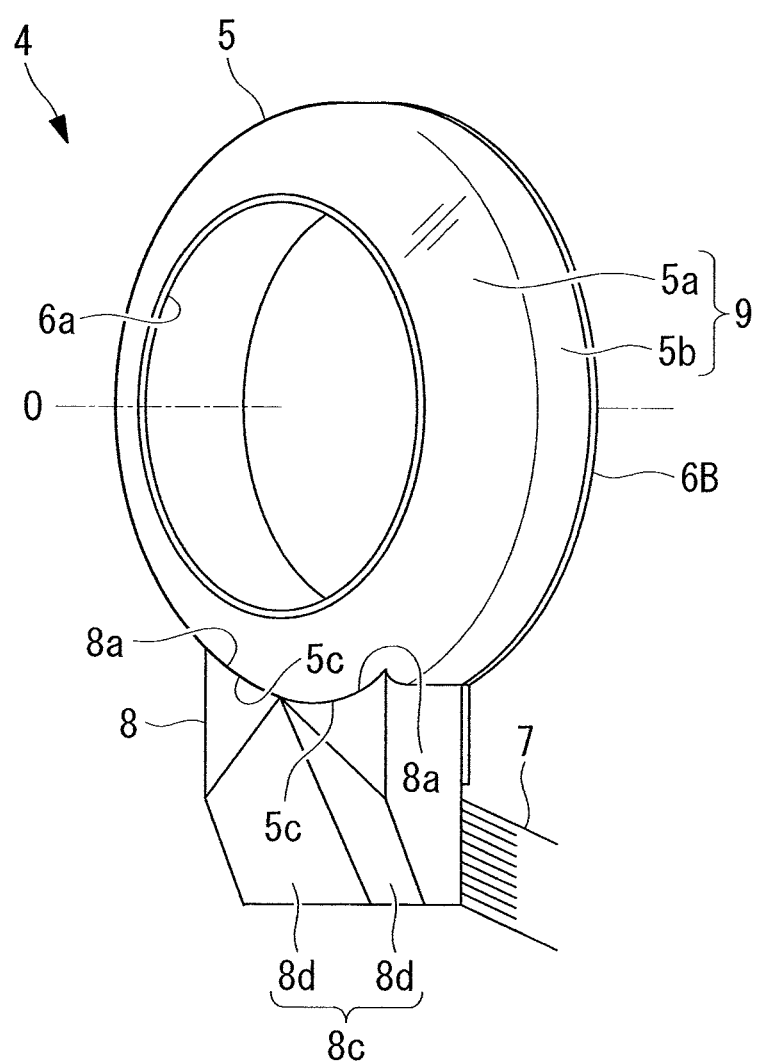
FIG. 5B is a perspective view of the illumination device in FIG. 5A.
Figure 5C:
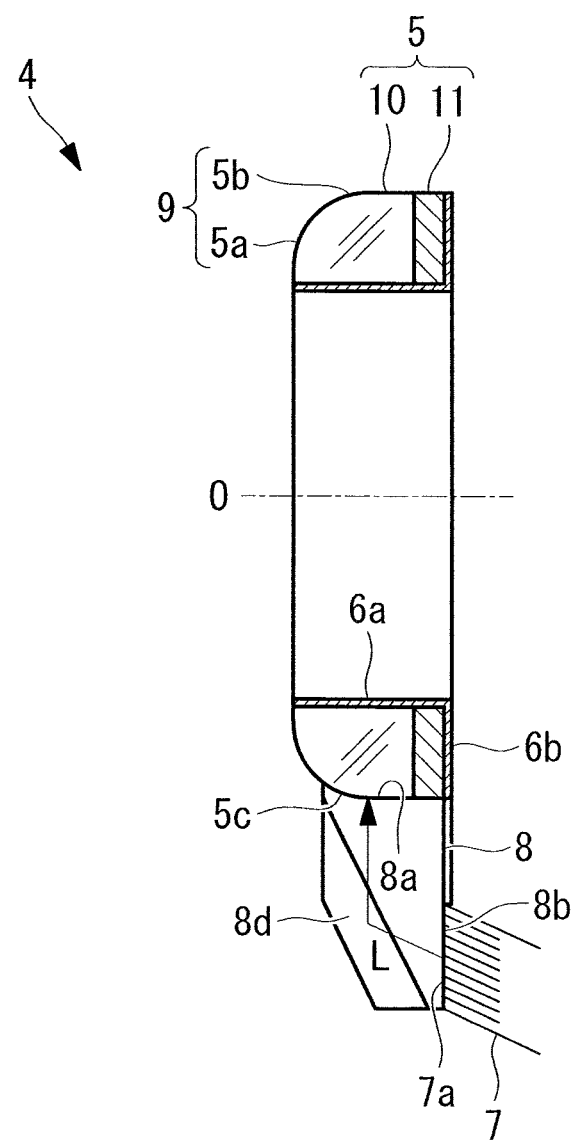
FIG. 5C is a cross-sectional view taken along line V-V in the illumination device in FIG. 5A.

In this case, by using the light-guiding member 8 shown in FIGS. 5A, 5B, and 5C, it is possible to introduce the illumination light L into the optical member 5 in two directions using the single light-guiding member 8.

The light-guiding member 8 in FIGS. 5A to 5C is a modification of the light-guiding member 8 in FIGS. 4A and 4B, and the deflecting portion 8c is formed of a pair of inclined surfaces 8d that are connected in a V-shape so as to be convex at the entrance portion 8b side. The angle formed by each inclined surface 8d and the central axis O and the angle formed between both inclined surfaces are calculated so that the illumination light L is reflected in the tangential direction of the optical member 5 along a plane perpendicular to the optical axis O, according to the entrance angle of the illumination light L at the entrance portion 8b from the light guide 7. The illumination light L that has entered the light-guiding member 8 via the entrance portion 8 from the emission end surface 7a of the light guide 7 is split into two by being reflected at the pair of inclined surfaces 8d along mutually differing tangential directions. The illumination light split into two is guided in mutually opposite circumferential directions inside the light-guiding member 8. Accordingly, it is possible to make the brightness in the circumferential direction of the illumination light L inside the optical member 5 more uniform.

Figure 6:
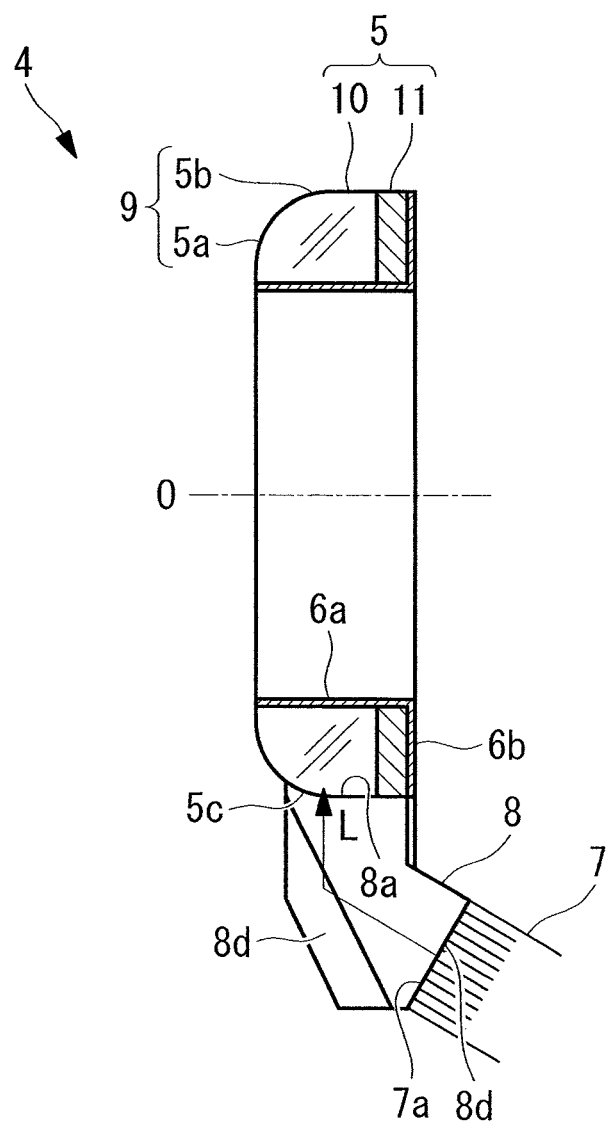
FIG. 6 is a cross-sectional view showing a modification of the illumination device in FIG. 5A.

In the configuration in which the illumination light L enters the light-guiding member 8 from the light guide 7 in approximately the central axis O direction, as shown in FIG. 4B, the emission end surface 7a of the light guide 7 may be perpendicular to the longitudinal axis of the light guide 7; as shown in FIG. 5C, it may be inclined with respect to the longitudinal axis of the light guide 7. In the case where the light-guiding member 8 having the V-shaped inclined surfaces 8d in FIGS. 5A to 5C is combined with the light guide 7 in which the emission end surface 7a is perpendicular to the longitudinal axis of the light guide 7, as shown in FIG. 6, it is preferable that the entrance portion 8b of the light-guiding member 8 be inclined with respect to the central axis O.

In some cases, the placement of the light guide 7 is restricted by a large number of members built into the distal end of the insertion section 2 in the endoscope 1, making it impossible to dispose the light guide 7 straight along the longitudinal direction of the insertion portion 2. In this case, as shown in FIGS. 5A to 6, by disposing the distal end surface of the light guide 7 at an angle relative to the central axis O, it is possible to efficiently dispose the light guide 7 in the distal end of the insertion portion 2.

Figure 7:
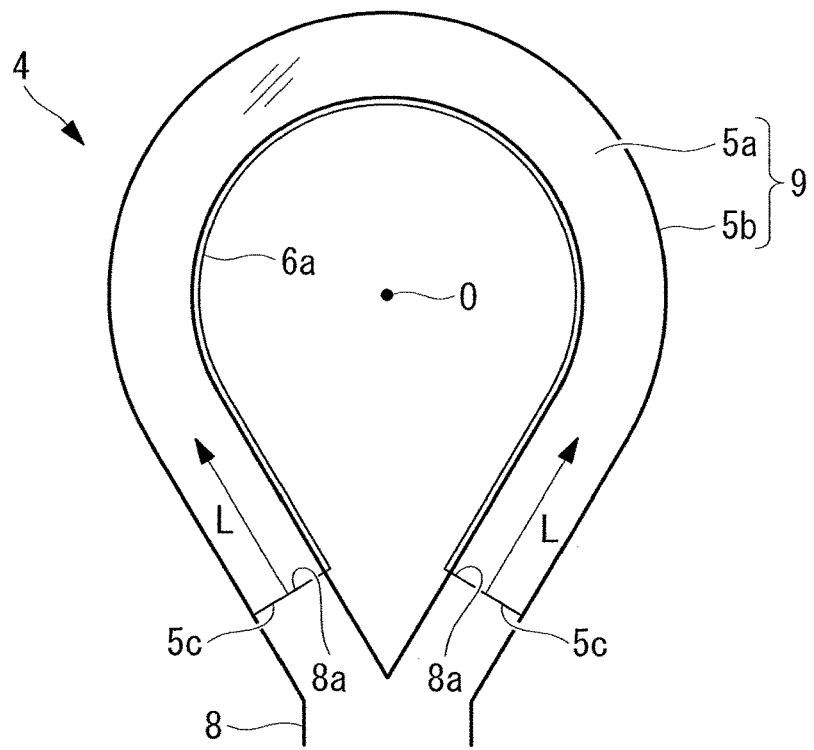
FIG. 7 is a front view, taken from the distal end side, showing another modification of the illumination device in FIG. 2A.
Figure 8:
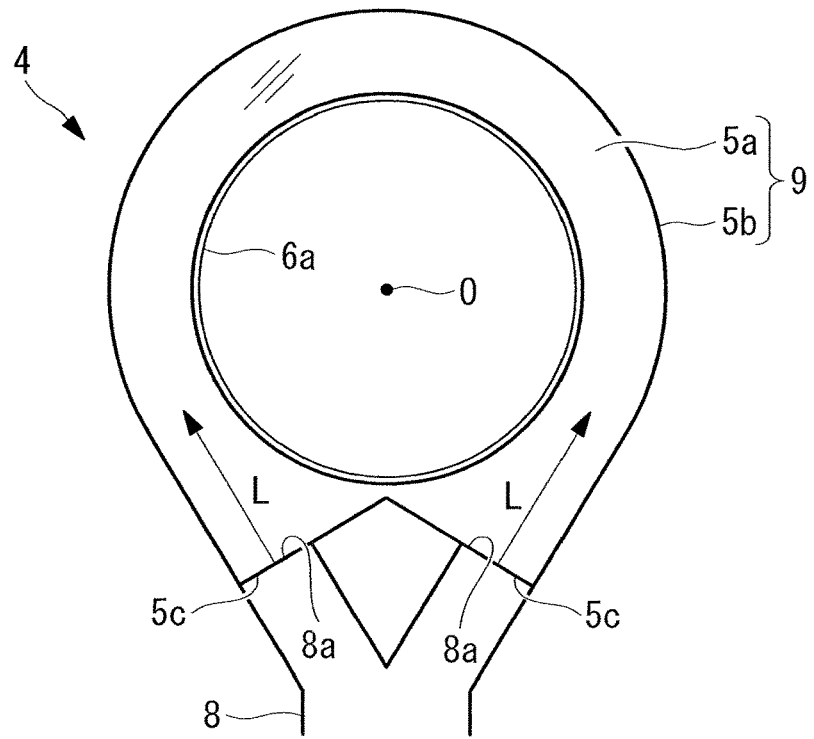
FIG. 8 is a front view, taken from the distal end side, showing another modification of the illumination device in FIG. 2A.

Moreover, in this embodiment, although the optical member 5 has been assumed to have a circular ring shape, instead of this, as shown in FIGS. 7 and 8, it may have a horseshoe shape in which a part thereof in the circumferential direction is cut out. As shown in FIG. 7, the optical member 5 may be cut at an intermediate position in the circumferential direction, and as shown in FIG. 8, only a portion thereof in the radial direction may be notched out in a V-shape, so as to be continuous in the circumferential direction.

In the optical members 5 in FIG. 7 and FIG. 8, the two end faces in the circumferential direction, pointing in the tangential direction, constitute light-entrance faces 5c, and by using a light-guiding member 8 having a pair of inclined surfaces 8d, like the light guiding member 8 in FIG. 5A and FIG. 5B, for example, the illumination light L enters from the two light-entrance faces 5c.

The above-described embodiment leads to the following invention.

A first aspect of the present invention is an illumination device comprising: an optical member that is provided with a circular ring-shaped or horseshoe-shaped light-guiding layer and diffusion layer, which are laminated in a central axis direction, the light-guiding layer having a light-entrance surface facing a tangential direction of the light-guiding layer; and a light-introducing member that is disposed at the radially outer side of the optical member and that introduces illumination light into the light-guiding layer from the light-entrance surface in the tangential direction; wherein the diffusion layer diffuses the illumination light entering from the light-guiding layer by volume scattering in the interior thereof, and the optical member is formed, at least, of one end surface in the central axis direction and has, at least, an emission surface that emits the illumination light emitted from the diffusion layer in the central axis direction.

According to the first aspect of the present invention, the illumination light that has entered the light-guiding layer in the tangential direction via the light-entrance surface from the light-introducing member is guided in the circumferential direction inside the light-guiding layer while undergoing repeated total reflection at the outer circumferential surface of the light-guiding layer and enters the diffusion layer. Part of the illumination light subjected to volume scattering in various directions inside the diffusion layer is emitted from the diffusion layer in the central axis direction and is emitted from the entirety of one end surface of the optical member in the form of a circular ring or horseshoe shape.

Therefore, the optical member is disposed coaxially with the optical axis of the imaging optical system at the outer side of the imaging optical system in the endoscope so that one end surface of the optical member is positioned at the most-distal end of the endoscope, whereby it is possible to illuminate the front viewing field of the imaging optical system.

In this case, the brightness of the illumination light is made uniform by diffusion due to volume scattering in the diffusion layer, and the illumination light is thereafter emitted from the emission surface, which includes, at least, the one end surface. Accordingly, the front viewing field of the imaging optical system can be illuminated with illumination light having uniform brightness.

In the above-described first aspect, the one end surface and an outer circumferential surface of the optical member may be smoothly continuous via a curved surface, and the emission surface may be formed of the one end surface and the outer circumferential surface.

By doing so, it is possible to eliminate brightness unevenness that occur in the illumination light due to the corner between the one end surface and the outer circumferential surface of the optical member. Furthermore, the illumination light that is guided in the circumferential direction inside the optical member has a contribution from a velocity component in the central axis direction during total reflection at the curved surface. Accordingly, entry to the diffusion layer of the illumination light guided in the circumferential direction in the light-guiding layer is facilitated, and it is possible to improve the emission efficiency of the illumination light from the emission surface.

The above-described first aspect may further comprise a reflecting portion that is disposed on the inner circumferential surface of the optical member and on the other end surface in the central axis direction thereof and that reflects the illumination light.

By doing so, it is possible to improve the emission efficiency from the emission surface of the illumination light that has entered the optical member.

In the above-described first aspect, the light-guiding layer and the diffusion layer may be laminated in order from the one end surface side.

By doing so, it is possible to further improve the brightness uniformity of the illumination light in the circumferential direction.

In the above-described first aspect, the outer circumferential surface of the diffusion layer may be exposed at the outer side and forms part of the emission surface.

By doing so, it is possible to effectively illuminate the lateral direction of the optical member with the illumination light directly emitted radially outward from the outer circumferential surface of the diffusion layer.

In the above-described first aspect, the diffusion layer may have a transparent medium that is transparent to the illumination light and a plurality of minute regions that are dispersed in the transparent medium and that have a refractive index different from that of the transparent medium.

By doing so, it is possible to easily construct a diffusion layer having a uniform diffusion effect with respect to the illumination light.

In the above-described first aspect, the minute regions may be formed of fine particles that satisfy conditional expressions (1) and (2) below:

$$100 \leq \phi \leq 500 \tag{100}$$

$$0.2 \leq \sigma \leq 0.5 \tag{2}$$

where $\phi$ is the particle diameter (nm) of the fine particles, and $\sigma$ is the particle density (weight %) of the fine particles in the transparent medium.

By doing so, it is possible to achieve both the propagation efficiency and the scattering efficiency of the illumination light in the diffusion layer, and a high diffusion effect of the illumination light is obtained by means of the diffusion layer.

In the above-described first aspect, the light-introducing member may include an emission portion disposed opposing the light-entrance surface; an entrance portion provided at the other end in the central axis direction thereof; and a deflecting portion that deflects the illumination light that has entered in approximately the central axis direction from the entrance portion, towards the emission portion in the tangential direction.

By doing so, it is possible to improve the degree of freedom in layout of the members, such as the light guide, for supplying the illumination light to the light-introducing member.

In the above-described first aspect, the deflecting portion may include a pair of inclined surfaces that are inclined with respect to the central axis and that are connected in a V-shape so as to be convex at the entrance portion side, and the pair of inclined surfaces may split the illumination light into two by deflecting the illumination light that has entered from the entrance portion in mutually different tangential directions.

By doing so, the illumination light split into two by the pair of inclined surfaces is guided inside the optical member in two mutually opposite directions, whereby the brightness uniformity of the illumination light can be further improved.

The above-described first aspect may further comprise: a light guide that has an emission end surface disposed opposite the entrance portion of the light-introducing member and that emits the illumination light towards the entrance portion from the emission end surface; wherein the emission end surface of the light guide may be disposed at an angle with respect to the central axis, and the entrance portion of the light-introducing member and the emission end surface of the light guide may be planar surfaces that are parallel to each other.

By doing so, the degree of freedom in layout of the light guide for supplying the illumination light to the light-introducing member can be improved.

In the above-described first aspect, the optical member and the diffusion layer may satisfy conditional expression (3) below:

$$0.075 \leq \tau/T \leq 0.3 \tag{3}$$

where $\tau$ is the thickness of the diffusion layer in the central axis direction, and T is the thickness of the optical member in the central axis direction.

By doing so, it is possible to achieve both a brightness-uniformizing effect in the circumferential direction of the illumination light with the light-guiding layer and a diffusion effect of the illumination light with the diffusion layer.

A second aspect of the present invention is an endoscope comprising: an imaging optical system; and any one of the above-described illumination devices, which is disposed around the imaging optical system so that the central axis becomes approximately aligned with an optical axis of the imaging optical system.

REFERENCE SIGNS LIST

1 endoscope
2 insertion portion
3 imaging optical system
4 illumination device
5 optical member
5a distal end surface
5b outer circumferential surface
6s, 6b reflecting portion
7 light guide
7a distal end surface (emission end surface)
8 light-guiding member (light-introducing member)
8a emission portion
8b entrance portion
8c deflecting portion 8d inclined surface
9 emission surface
10 light-guiding layer
11 diffusion layer
O central axis
O' optical axis
L illumination light

The invention claimed is:

1. An illumination device comprising:
an optical member comprising a circular ring-shaped or horseshoe-shaped light-guiding layer and diffusion layer, which are laminated along a central axis direction, the light-guiding layer having a light-entrance surface facing along a tangential direction of the light-guiding layer;
a light-introducing member that is disposed at a radially outer side of the optical member and that introduces illumination light into the light-guiding layer from the light-entrance surface in the tangential direction; and
a reflecting portion configured to reflect the illumination light;
wherein the diffusion layer diffuses the illumination light entering from the light-guiding layer by volume scattering in an interior of the diffusion layer;
wherein the diffusion layer comprises a transparent medium that is transparent to the illumination light and a plurality of minute regions that are dispersed in the transparent medium and that have a refractive index different from that of the transparent medium;
wherein the optical member includes an end surface in the central axis direction at least as an emission surface that emits the illumination light emitted from the diffusion layer in the central axis direction; and
wherein the light-guiding layer, the diffusion layer, and the reflecting portion are arranged such that the diffusion layer is laminated on the light-guiding layer on an opposite side from said end surface of the optical member in the central axis direction, and such that the diffusion layer is positioned between the light-guiding layer and the reflecting portion.

2. The illumination device according to claim 1, wherein:
said end surface of the optical member in the central axis direction and an outer circumferential surface of the optical member are smoothly continuous via a curved surface; and
the emission surface comprises both said end surface and the outer circumferential surface.

3. The illumination device according to claim 1, further comprising an additional reflecting portion that is disposed on an inner circumferential surface of the optical member and that is configured to reflect the illumination light.

4. The illumination device according to claim 1, wherein an outer circumferential surface of the diffusion layer is exposed at the outer side of the optical member and forms part of the emission surface.

5. The illumination device according to claim 1, wherein the minute regions are formed of fine particles that satisfy conditional expressions (1) and (2) below:

$$100 \leq \phi \leq 500, \text{ and} \tag{1}$$

$$0.2 \leq \sigma \leq 0.5, \tag{2}$$

where $\phi$ is a particle diameter (nm) of the fine particles, and $\sigma$ is a particle density (weight %) of the fine particles in the transparent medium.

6. The illumination device according to claim 1, wherein the light-introducing member comprises:
an emission portion opposing the light-entrance surface;
an entrance portion; and
a deflecting portion that deflects the illumination light that has entered in approximately the central axis direction from the entrance portion, towards the emission portion in the tangential direction;
wherein the entrance portion is provided at an opposite side of the light-introducing member in the central axis direction from the deflecting portion.

7. The illumination device according to claim 6, wherein:
the deflecting portion includes a pair of inclined surfaces that are inclined with respect to the central axis and that are connected in a V-shape so as to be convex at an entrance portion side, and
the pair of inclined surfaces split the illumination light into two by deflecting the illumination light that has entered from the entrance portion in mutually different tangential directions.

8. The illumination device according to claim 6, further comprising:
a light guide that has an emission end surface disposed opposite the entrance portion of the light-introducing member and that emits the illumination light towards the entrance portion from the emission end surface;
wherein the emission end surface of the light guide is disposed at an angle with respect to the central axis, and
wherein the entrance portion of the light-introducing member and the emission end surface of the light guide are planar surfaces that are parallel to each other.

9. The illumination device according to claim 1, wherein the optical member and the diffusion layer satisfy conditional expression (3) below:

$$0.075 \leq \tau/T \leq 0.3, \tag{3}$$

where $\tau$ is a thickness of the diffusion layer in the central axis direction, and T is a thickness of the optical member in the central axis direction.

10. An endoscope comprising:
an imaging optical system; and
the illumination device according to claim 1, which is disposed around the imaging optical system so that the central axis is approximately aligned with an optical axis of the imaging optical system.

11. An optical element for illumination comprising:
a ring-shaped portion that has a ring shape and comprises a light-guiding layer, a diffusion layer, and an emission surface, the light-guiding layer and the diffusion layer being laminated along a direction of a central axis of the ring-shaped portion, and the emission surface including an end surface facing along the direction of the central axis;
an introducing portion that is formed so as to protrude in a direction away from the central axis and that includes a light-receiving surface for receiving an illumination light; and
a reflecting portion configured to reflect the illumination light;
wherein the illumination light introduced from the light-receiving surface to the light-guiding layer via the introducing portion is diffused by volume scattering in the diffusion layer to be emitted from the emission surface;
wherein the diffusion layer comprises a transparent medium that is transparent to the illumination light and a plurality of minute regions that are dispersed in the transparent medium and that have a refractive index different from that of the transparent medium; and wherein the light-guiding layer, the diffusion layer, and the reflecting portion are arranged such that the diffusion layer is laminated on the light-guiding layer on an opposite side from said end surface of the ring-shaped portion in the central axis direction, and such that the diffusion layer is positioned between the light-guiding layer and the reflecting portion.

12. The optical element according to claim 11, wherein the light-receiving surface is disposed on the opposite side from said end surface.

13. The optical element according to claim 12, wherein:
the introducing portion includes a protrusion disposed at a distal end of the introducing portion and disposed on the opposite side from said end surface; and
the protrusion is provided with the light-receiving surface.

14. The optical element according to claim 11, further comprising another reflecting portion that is disposed on an inner circumferential surface of the ring-shaped portion and that is configured to reflect the illumination light.

15. The optical element according to claim 11, wherein an outer circumferential surface of the diffusion layer is exposed at an outer side of the ring-shaped portion and forms part of the emission surface.

16. The optical element according to claim 11, wherein the minute regions are formed of fine particles that satisfy conditional expressions (1) and (2) below:

$$100 \le \phi \le 500, \text{ and} \quad (1)$$

$$0.2 \le \sigma \le 0.5, \quad (2)$$

where $\phi$ is a particle diameter (nm) of the fine particles, and $\sigma$ is a particle density (weight %) of the fine particles in the transparent medium.

17. The optical element according to claim 11, wherein the introducing portion includes a deflecting portion that deflects the illumination light that has entered from the light-receiving surface towards the ring-shaped portion.

18. The optical element according to claim 17, wherein:
the deflecting portion includes a pair of inclined surfaces that are inclined with respect to the central axis and that are connected in a V-shape so as to be convex at a light-receiving surface side; and
the pair of inclined surfaces split the illumination light into two by deflecting the illumination light that has entered from the light-receiving surface toward the ring-shaped portion in mutually different directions.

19. The optical element according to claim 11, wherein the optical element satisfies conditional expression (3) below:

$$0.075 \le \tau/T \le 0.3, \quad (3)$$

where $\tau$ is a thickness of the diffusion layer in the direction of the central axis, and T is a thickness of the ring-shaped portion in the direction of the central axis.

20. An illumination device comprising:
the optical element according to claim 11; and
a light guide that has an emission end surface disposed opposite the light-receiving surface of the introducing portion and that emits the illumination light from the emission end surface.

21. The illumination device according to claim 20, wherein:
the emission end surface of the light guide is disposed at an angle with respect to the central axis, and
the light-receiving surface of the introducing portion is an inclined surface parallel to the emission end surface of the light guide.

22. An endoscope comprising:
an imaging optical system; and
the illumination device according to claim 20, which is disposed around the imaging optical system so that the central axis is approximately aligned with an optical axis of the imaging optical system.

* * * * *